United States Patent
Norman

(10) Patent No.: US 7,205,422 B2
(45) Date of Patent: Apr. 17, 2007

(54) VOLATILE METAL β-KETOIMINATE AND METAL β-DIIMINATE COMPLEXES

(75) Inventor: John Anthony Thomas Norman, Encinitas, CA (US)

(73) Assignee: Air Products and Chemicals, Inc., Allentown, PA (US)

(*) Notice: Subject to any disclaimer, the term of this patent is extended or adjusted under 35 U.S.C. 154(b) by 159 days.

(21) Appl. No.: 11/111,452

(22) Filed: Apr. 21, 2005

(65) Prior Publication Data

US 2006/0145142 A1  Jul. 6, 2006

Related U.S. Application Data

(60) Provisional application No. 60/640,338, filed on Dec. 30, 2004.

(51) Int. Cl.
- C07F 1/08 (2006.01)
- C07F 15/00 (2006.01)
- H01L 29/08 (2006.01)
- H01L 35/24 (2006.01)
- C23C 16/00 (2006.01)

(52) U.S. Cl. .............. 556/32; 556/1; 556/11; 556/137; 556/138; 427/248.1; 427/255.19; 257/40

(58) Field of Classification Search .......... 556/1, 556/11, 32, 137, 138; 427/248.1, 255.19; 257/40

See application file for complete search history.

(56) References Cited

U.S. PATENT DOCUMENTS

| | | | |
|---|---|---|---|
| 5,098,516 A | 3/1992 | Norman et al. | |
| 6,538,147 B1 | 3/2003 | Choi | |
| 6,552,209 B1 | 4/2003 | Lei et al. | |
| 6,818,783 B2 | 11/2004 | Norman et al. | |
| 6,869,876 B2 | 3/2005 | Norman et al. | |
| 7,132,556 B2* | 11/2006 | Benvenuti et al. | ............ 556/32 |
| 2003/0129308 A1 | 7/2003 | Chen et al. | |
| 2004/0247905 A1 | 12/2004 | Bradley et al. | |
| 2005/0227007 A1* | 10/2005 | Bradley et al. | ............ 427/305 |

FOREIGN PATENT DOCUMENTS

| | | |
|---|---|---|
| JP | 06145986 | 11/1992 |
| JP | 2002 193988 A2 | 7/2002 |
| WO | 200168580 A1 | 3/2000 |
| WO | WO 200166347 A1 | 3/2000 |

OTHER PUBLICATIONS

Martensson, et al., "Atomic Layer Epitaxy of Copper", J. Electrochem. Soc., vol. 145, No. 8, Aug. 1998, pp. 2926-2931.

Awaya, et al., "Double-Level Copper Interconnections Using Selective Cooper CVD", Journal of Electronic Materials, vol. 21, No. 10, 1992, pp. 959-964.

Fine, et al., "Organometallic Chemical Vapor Deposition of Copper From A New Organometallic Precursor", Mat. Res. Soc. Symp. Proc., vol. 204, 1991, pp. 415-420.

Beach, et al., "Low-Temperature Chemical Vapor Deposition of High-Purity Copper from an Organometallic Source", Chem. Mater. 1990, 2, 216-219.

(Continued)

Primary Examiner—Porfirio Nazario-Gonzalez
(74) Attorney, Agent, or Firm—Rosaleen P. Morris-Oskanian; Joseph D. Rossi

(57) ABSTRACT

Metal ketoiminate or diiminate complexes, containing copper, silver, gold, cobalt, ruthenium, rhodium, platinum, palladium, nickel, osmium, or indium, and methods for making and using same are described herein. In certain embodiments, the metal complexes described herein may be used as precursors to deposit metal and metal-containing films on a substrate through, for example, atomic layer deposition or chemical vapor deposition conditions.

18 Claims, 1 Drawing Sheet

OTHER PUBLICATIONS

Kroger, et al., "Properties of Copper Films Prepared by Chemical Vapor Deposition for Advanced Metallization of Microelectronic Devices", Journal of the Electrochemical Society, 146 (9) 3248-3254 (1999).

Shin, et al., "Synthesis of Volatile, Fluorinated B-Ketoiminato Copper(i) Complexes", J. Chem. Soc., Chem. Commun., 1992, pp. 217-219.

CA Selects: Chemical Vapor Deposition (CVD), Issue 7, 1996, p. 16.

Bouquillon, Sandrine, et al., "simultaneous genertion of anionic and neutral palladium (II) complexes from .eta.3-allylpalladium chloride dimer and fluorinated.beta.-enaminones", European Journal of Organic Chemistry, (24), 4717-4720, (2003).

Tung, Yeng-Lien, et al., "Synthesis and Characterization of Allyl (.beta.-ketoiminato)palladium (I) Complexes: New Precursors for Chemical Vapor Deposition of Palladium Thin Films", Organometallics, 18(5), 864-869, (1998).

Edwards, Dennis A., et al., "Aerosol-assisted chemical vapour deposition (AACVD) of silver films from triphenylphosphine adducts of silver .beta.-diketonates and .beta.-diketoiminates, including the structure of [Ag(hfac)(PPh3)]", Journal of Materials Chemistry (1999), 9(8), 1771-1780.

European Search Report No. 05028247.4-2117, dated Apr. 7, 2006.

* cited by examiner

VOLATILE METAL β-KETOIMINATE AND METAL β-DIIMINATE COMPLEXES

CROSS-REFERENCE TO RELATED APPLICATIONS

This application claims the benefit of U.S. Provisional Application No. 60/640,338, filed 30 Dec. 2004.

BACKGROUND OF THE INVENTION

The semiconductor industry uses metal-containing interconnects, such as copper (Cu), in electronic devices such as, for example, state of the art microprocessors. The metal-containing interconnects, which may be embedded fine metal lines, form the three dimensional grid upon which millions of transistors at the heart of the microprocessor can communicate and perform complex calculations. In these and other applications, copper or alloys thereof may be chosen over other metals such as, for example, aluminum because copper is a superior electrical conductor, thereby providing higher speed interconnections of greater current carrying capability.

Interconnect pathways within electronic devices are typically prepared by the damascene process, whereby photolithographically patterned and etched trenches and vias in the dielectric insulator are coated with a conformal thin layer of a diffusion barrier material. A diffusion barrier layer is typically used in conjunction with a metal or copper layer to prevent detrimental effects caused by the interaction or diffusion of the metal or copper layer with other portions of the integrated circuit. Exemplary barrier materials include, but are not limited to, titanium, tantalum, tungsten, chromium, molybdenum, zirconium, ruthenium, vanadium, and/or platinum as well as carbides, nitrides, carbonitrides, silicon carbides, silicon nitrides, and silicon carbonitrides of these materials and alloys comprising same. In certain processes, such as when, for example, the interconnect comprises copper, the diffusion barrier layer may be coated with a thin 'seed' or 'strike' layer of copper, prior to completely filling in the features with pure copper. In still other cases, the seed layer of copper may be replaced by—or used in addition to—an analogous cobalt or similar conducting thin film 'glue' layer. Excess copper may then removed by the process of chemical mechanical polishing. Since the smallest features to be filled can be less than 0.2 microns wide and over 1 micron deep, it is preferable that the copper seed layer, copper glue layer and/or the diffusion barrier layers be deposited using metallization techniques that are capable of evenly filling these features, without leaving any voids, which could lead to electrical failures in the finished product.

Numerous methods such as ionized metal plasma (IMP), physical vapor deposition (PVD), chemical vapor deposition (CVD), atomic layer deposition (ALD), plasma-assisted chemical vapor deposition (PACVD), plasma-enhanced chemical vapor deposition (PECVD), electroplating, and electroless plating have been used to deposit metal-containing layers such as the metallization, diffusion barrier, and/or other layers. Among them, CVD and ALD methods using one or more organometallic precursors may be the most promising methods because these methods provide excellent step coverage for high aspect ratio structures and good via filling characteristics. In a typical CVD process, a vapor of a volatile organometallic precursor containing the desired metal is introduced to a substrate surface whereupon a chemical reaction occurs in which a thin film containing the metal as a compound or as a pure element is deposited on the substrate. Since the metal is typically delivered in a vapor form as a volatile precursor, it can access both vertical and horizontal surfaces to provide an evenly distributed thin film. In a typical ALD process, a volatile organometallic precursor is alternately pulsed into a reactor with a reagent gas such that self-limiting alternating monolayers of precursor/reagent are deposited on the substrate wherein the monolayers react together to form a metal film or a metal-containing film which is subsequently reduced to metal or used as deposited. For example, if a copper organometallic precursor was reacted with a suitable oxidant in an ALD process, the resulting cuprous oxide or cupric oxide monolayer or multilayer could be used for semiconductor applications or reduced to copper metal.

For copper thin films, some of the same precursors suitable for CVD and other depositions may also be suitable as ALD precursors. In certain applications, it may be preferable that the precursor be highly volatile, deposit copper films that are substantially pure (i.e., have a purity of about 95% or about 99% or greater copper), and/or minimize the introduction of potentially contaminating species into the reaction chamber or onto the diffusion barrier or other underlying surfaces. Further, in these applications, it may be preferable that the copper film exhibits good adhesion to the diffusion barrier layer because poor adhesion may lead to, inter alia, delamination of the copper film during chemical mechanical polishing.

Several organometallic precursors have been developed to deposit low electrical resistivity copper films by the aforementioned processes, particularly CVD or ALD processes. Two of often-used families of copper organometallic precursors that have been studied extensively are the Cu(I) and Cu(II) precursors. One commonly used Cu(I) precursor is a precursor having the formula "Cu(I)(hfac)(W)" precursor where "hfac" represents the 1,1,1,5,5,5-hexafluoro-2,4-pentanedionate anion and (W) represents a neutral stabilizing ligand, such as, for example, an olefin, an alkyne, or a trialkylphosphine. One particular example of a Cu(I) precursor having the above formula is 1,1,1,5,5,5-hexafluoro-2,4-pentanedionato-copper (I) trimethylvinylsilane (hereinafter Cu(hfac)(tmvs)), which is sold under the trademark CUPRASELECT™ by Air Products and Chemicals, Inc. of Allentown, Pa., the assignee of the present application. These Cu(I) precursors can deposit films via a disproportionation reaction whereby two molecules of the precursor react on a heated substrate surface to provide copper metal, two molecules of free ligand (W), and the volatile byproduct $Cu^{(+2)}(hfac)_2$. Equation (1) provides an example of a disproportionation reaction:

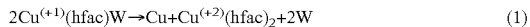

$$2Cu^{(+1)}(hfac)W \rightarrow Cu + Cu^{(+2)}(hfac)_2 + 2W \qquad (1)$$

In CVD depositions, the disproportionation reaction illustrated in Equation (1) is typically run at a temperature of around 200° C.; however, other temperatures may be used depending upon the deposition process. As Equation (1) illustrates, the $Cu^{(+2)}(hfac)_2$ constitutes a byproduct from the reaction and may need to be removed from the reaction chamber.

Yet another type of Cu(I) precursor is a precursor having the formula "(Y)Cu(Z)". In these particular Cu(I) precursors, "Y" is an organic anion and "Z" is a neutral stabilizing ligand, such as, for example, trialkyphosphine. An example of such a precursor is $CpCuPEt_3$, where Cp is cyclopentadienyl and $PEt_3$ is triethylphoshine. Under typical CVD conditions, two of these precursor molecules may react on a wafer surface, whereby the two stabilizing trialkyphosphine Z ligands become disassociated from the copper centers, the two (Y) ligands become coupled together, and the copper (I) centers are reduced to copper metal. The overall reaction is shown below in Equation (2).

$$2(Y)Cu(Z) \rightarrow 2Cu + (Y-Y) + 2(Z) \quad (2)$$

However, in certain instances, this type of chemistry may present problems because the released trialkylphosphine ligands may contaminate the reaction chamber and act as undesired N-type silicon dopants.

As mentioned previously, yet another type of precursor used to deposit copper-containing films is Cu(II) precursors. Unlike the Cu(I) precursors, the Cu(II) precursors require the use of an external reducing agent such as, for example, hydrogen or alcohol to deposit copper films that are largely free of impurities. An example of a typical Cu(II) precursor has the chemical formula $Cu(II)(Y)_2$ wherein (Y) is an organic anion. Examples of this type of precursor include, but are not limited to, Cu(II)bis(β-diketonates), Cu(II) bis (β-diimine), and Cu(II) bis(β-ketoimine) compounds. Equation (3) provides an illustration of a deposition reaction wherein hydrogen is used as the reducing agent.

$$Cu(II)(Y)_2 + H_2 \rightarrow Cu + 2YH \quad (3)$$

The Cu(II) precursors are typically solids and the temperatures required for film deposition are typically above 200° C.

While copper precursors are widely used as interconnects, other metals or alloys are used as thin films in electronic devices. Examples of such metals include silver (Ag), gold (Au), cobalt (Co), ruthenium (Ru), rhodium (Rh), platinum (Pt), palladium (Pd), nickel (Ni), osmium (Os), indium (In), and alloys thereof.

BRIEF SUMMARY OF THE INVENTION

Metal complexes, and methods for making and using same, such as for example as a precursor in a deposition process, are described herein. In one aspect, there is provided a metal complex represented by formula (I):

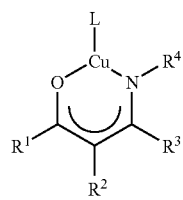

wherein M is a metal selected from Cu, Au, Ag, Co, Ru, Rh, Pt, In, Pd, Ni, and Os;

wherein X is selected from oxygen and $NR^5$;

wherein $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;

wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;

wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond.

In another aspect, there is provided a process for depositing a film comprising metal on a substrate comprising: contacting the substrate with a metal complex having the above formula (I) wherein the contacting is conducted under conditions sufficient for the complex to react and form the film.

In a further aspect, there is provided an electronic device comprising a film comprising metal wherein the film is deposited using a metal complex having the above formula (I).

In yet another aspect, there is provided a method of making a metal complex having the above formula (I) where X is oxygen comprising: preparing a primary amine having a formula $H_2NR^4L$ wherein $R^4$ and L are as described above; condensing the primary amine with a β-diketone having a formula $R^1C(O)CHR^2C(O)R^3$ to form an intermediate β-ketoimine product having a formula $R^1C(O)CHR^2CNR^4LR^3$ wherein $R^1$, $R^2$, $R^3$, $R^4$, and L are as described above and deprotonating the β-ketoimine intermediate product using a base in the presence of a metal source to form the metal complex.

In a further aspect, there is provided a method of making a metal complex having the above formula (I) wherein X is oxygen comprising: condensing an amine having a formula $H_2NR^4$ with a β-diketone having a formula $R^1C(O)CHR^2C(O)R^3$ to form a first intermediate β-ketoimine product having a formula $R^1C(O)CHR^2CN(R^4)R^3$ wherein $R^1$, $R^2$, $R^3$, and $R^4$ are as described above; attaching a ligand (L) to $R^4$ in the first intermediate β-ketoimine product to provide a second intermediate β-ketoimine product having a formula $R^1C(O)CHR^2CNR^4LR^3$ wherein $R^1$, $R^2$, $R^3$, $R^4$, and L is as described above; deprotonating the second β-ketoimine intermediate product using a base in the presence of a metal source to form the metal complex.

DETAILED DESCRIPTION OF THE INVENTION

Figure 1:
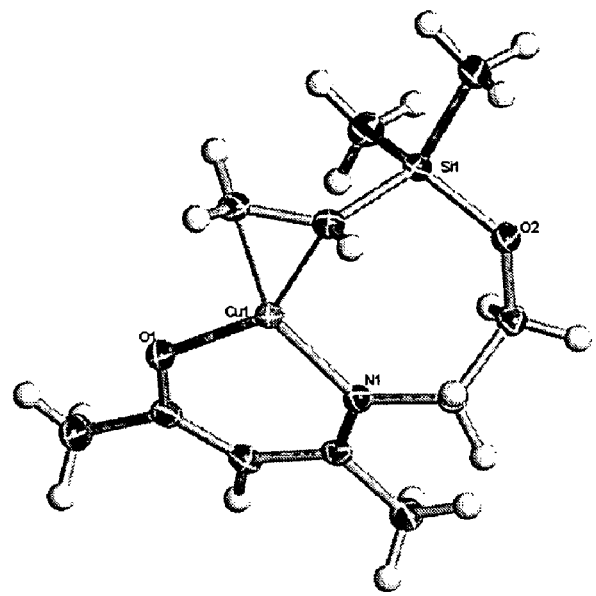
FIG. 1 provides an exemplary structure of one of the metal complexes described herein or $Cu(MeC(O)CHC(NCH_2CH_2OSiMe_2(C_2H_3))Me)$ complex.

Metal complexes, particularly copper (I) complexes, and methods for making and using same are described herein. The metal complexes may be used, for example, as precursors to deposit metal films or metal-containing films via a variety of deposition processes, including CVD or ALD processes.

The metal complexes described herein provide one or more advantageous properties due to their unique structure. The combination of relatively high thermal stability and relatively high chemical reactivity that the metal complexes described herein exhibit—compared to other organometallic metal precursors—may be desirable for CVD and ALD, particularly ALD precursors. For CVD systems, it is desirable that the reaction of the precursor occur only on the heated substrate surface rather than during vapor delivery and/or in the processing chamber. For ALD systems, it is desirable that the metal precursor react at specific sites while not suffering unwanted thermal degradation during vapor delivery and/or in the processing chamber. The metal complexes described herein have a relatively high thermal stability which allows them to be delivered as a stable vapor into a CVD or ALD reactor. In this connection, it is believed that since ligand L is directly attached to the ketoimine or the diimine ligand, it is not able to readily disassociate from the metal center (M) as a free molecule, tending to keep ligand L coordinated to the metal center under conditions of low pressure and heat which would typically be sufficient to fully disassociate ligand L. This in contrast to analgous complexes where L is bonded only to the metal center. In alternative embodiments, substituent group $R^4$, which associates the ketoimine or the diimine ligand with the ligand L, can be chemically engineered such that under the correct process conditions this association can be broken or disassociated to effectively release the ligand L. The term "associate" as used herein means to join the ketoimine or diimine ligand with ligand L and can include, but is not limited to, a chemical bond (e.g., covalent bond, hydrogen bond, etc.) an electrostatic attraction, Lewis acid-Lewis base interaction, and/or other means. In these embodiments and under certain processing conditions sufficient to release ligand L, it may allow, for example, the complex to disproportionate to give a metal film or a metal-containing film. Further, the disassociation of $R^4$ with ligand L may reduce the precursor into lower molecular weight units which are more readily desorbed during processing, for example, in a CVD or ALD reactor. For instance, if the precursor is fully reacted with water then the result of the disassociation would be copper oxide growth along with the release of hydrolyzed small molecular weight volatile ligand fragments. For example, metal complex $Cu(Me(C(O)CHC(NCH_2CH_2NMeSiMe_2(C_2H_3))Me)$ (where the $C_2H_3$ group within the complex represents a vinyl group) reacts with water to yield solid cuprous oxide, $MeC(O)CH_2C(NCH_2CH_2NMeH)Me$, and $C_2H_3Me_2SiOH$, the latter of which couples to provide tetramethyldivinyldilsiloxane.

Another unique feature of these complexes is its ability to provide a metal center which is more sterically exposed on one face of the precursor. Typical β-ketoimine or β-diketone olefin compounds are flat molecules where the coordinating diketonate or ketoiminate anion, the metal center, and olefin all lie within the same plane. By contrast, the complexes described herein may allow for the complex's plane of coordination to become convexly bowed pushing the metal center more towards the underside of the complex thereby allowing it to be more exposed and accessible to surfaces and reagent molecules. For instance, in exemplary metal complex $Cu(MeC(O)CHC(NCH_2CH_2OSiMe_2(C_2H_3))Me)$, the β-ketoiminate chelate ring is tilted approximately seven degrees away from the copper olefin coordination triangle thereby exposing the copper more on the underside of the molecule. This exposure and hence greater steric access may be important for certain ALD and CVD type processes because it can help the copper atom contained therein to adsorb onto the substrate surface. Further, by controlling the nature and the length of the $R^4$ association to ligand L, one can develop metal precursors that are relatively strained in their conformation to provide exposed metal centers. Releasing this strain by chemically breaking or disassociating the $R^4$ link with ligand L allows for relatively high reactivity. In other words, by adjusting the structure of these precursors, it should be possible to build complexes with internal strain that can be relieved by breaking the $R^4$ link to drive the molecule's decomposition into small volatile organic units while at the same time providing a sterically exposed metal center for high surface reactivity and metal deposition.

The metal complexes described herein have the following formula (I):

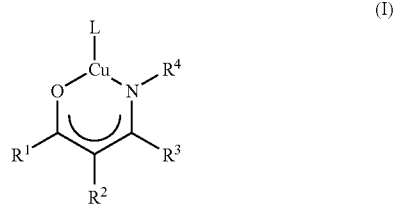

(I)

In formula (I), M is a metal selected from Cu, Au, Ag, Co, Ru, Rh, Pt, In, Pd, Ni, and Os. In certain embodiments, metal atom M is copper. In formula (I), X can be oxygen thereby forming a ketoiminate complex, or alternatively X can be $NR^5$ thereby forming a diiminate complex. In formula (I), substituents $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms. In formula (I), substituent $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl comprising from 6 to 12 carbon atoms; an alkoxy comprising from 1 to 20 carbon atoms; and an amide comprising from 1 to 20 carbon atoms and wherein $R^4$ has a hydrogen, an atom, or a group removed to associate with L. Further, in formula (I), L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, vinyl, an aryl, or an amide comprising from 1 to 20 carbon atoms and $R^{13}$ is each independently a hydrogen or an alkyl comprising from 1 to 20 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom, an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl, amide, or alkoxy comprising from 1 to 20 carbon atoms; and an aryl group comprising from 6 to 12 carbon atoms and wherein L has a hydrogen, an atom, or a group removed to associate with $R^4$.

The term "alkyl" as used herein includes straight chain, branched, or cyclic alkyl groups, comprising from 1 to 20 carbon atoms, or from 1 to 10 carbon atoms. Exemplary alkyl groups include methyl, ethyl, n-propyl, isopropyl, n-butyl, isobutyl, sec-butyl, tert-butyl, tert-amyl, n-pentyl, n-hexyl, cyclopentyl, and cyclohexyl. The term "alkyl" applies also to alkyl moieties contained in other groups such as fluoroalkyl, haloalkyl, alkylaryl, or arylalkyl. The term "aryl" as used herein comprises 6 to 12 member carbon rings having aromatic character. Exemplary aryl groups include phenyl and napthyl groups. The term "alkyl-substituted aryl" applies to aryl moieties that are substituted with alkyl. Exemplary alkyl-substituted aryl groups include tolyl and xylyl groups. The term "halo" and "halogen" include fluorine, chlorine, bromine, or iodine. The term "fluoroalkyl" applies to alkyl moieties wherein one or more of its hydrogen atoms are replaced by a fluorine halogen atom, may be partially or fully fluorinated, and includes straight chain, branched or cyclic fluorinated alkyl groups comprising from 1 to 20 carbon atoms, or from 1 to 10 carbon atoms. Exemplary fluoroalkyl groups include —$CF_3$, —$CF_2CF_3$, —$CH_2CF_3$, —$CF_2CFH_2$, or —$CH_2CF_2CF_3$. In certain embodiments, some of the groups discussed herein may be substituted with one or more other elements such as, for example, a halogen atom or other heteroatoms such as O, N, Si, or S.

In formula (I), substituent $R^4$ is selected such that it can associate with the ligand L. Further, ligand L is selected such that it can associate with $R^4$. It is believed that both ligand L and substituent $R^4$ have a hydrogen, atom, or group removed that allows $R^4$ and L to associate thereby connecting the ketoimine or diimine ligand of the complex with ligand L. In this connection, when L is silylalkene, one of its bonds is available to associate with $R^4$. One exemplary embodiment is shown in FIG. 1 or Cu(MeC(O)CHC (NCH$_2$CH$_2$OSiMe$_2$(C$_2$H$_3$))Me). In this embodiment, X is oxygen, L has the formula H$_2$C=CHSiMe$_2$, $R^4$ is OCH$_2$CH$_2$, $R^3$ is hydrogen, and $R^1$ and $R^2$ are both methyl groups. In another embodiment where X is $NR^5$, $R^5$ and L can associate. In this embodiment, both ligand L and substituent $R^5$ have a hydrogen, atom, or group removed that allows $R^5$ and L to associate in the same fashion as $R^4$ and L are associated.

In certain embodiments, substituent $R^4$ may also be connected to substituents $R^1$, $R^2$ and/or $R^3$. In these embodiment, substituent $R^4$ can only connect with substituents $R^1$, $R^2$ and/or $R^3$ when $R^1$, $R^2$ and/or $R^3$ are neither a hydrogen atom, a halogen atom, nor the nitro group NO$_2$.

In certain embodiments of the complex described herein, X is $NR^5$ and $R^5$ can be any of the groups or atoms described above for $R^1$, $R^2$, or $R^3$. In these embodiments, ligand (L), or alternatively an additional ligand (L) which can be any of the groups or atoms described above, can also be attached to substituent $R^5$ as well as substituent $R^4$. In these embodiments, it is believed that at least one ligand L has, for example, an available valence with which to associate with $R^5$ thereby connecting the diimine ligand of the complex with ligand L. In this or other embodiments, substituent $R^5$ can also be connected to any one or all of substituents $R^1$, $R^2$, $R^3$, and/or $R^4$ to form cyclic structures. In the latter embodiment, substituent $R^5$ connects with substituents $R^1$, $R^2$ and/or $R^3$ only when $R^1$, $R^2$ and/or $R^3$ are neither a hydrogen atom, a halogen atom, nor the nitro group NO$_2$, or alternatively when $R^5$ is a hydrogen atom.

In certain embodiments, substituent $R^4$, and/or optionally substituent $R^5$ if X is $NR^5$, may be adjusted such that the ligand L coordinates to the metal center of an adjacent complex rather than to its own metal center. In these embodiments, other complexes such as, but not limited to, dimeric, trimeric, and tetrameric complexes can form.

In certain embodiments, any one or all of substituents $R^1$, $R^2$, and $R^3$ can be independently connected to form cyclic structures. In certain embodiments, $R^1$ and $R^2$ and/or $R^2$ and $R^3$ can be independently connected to form cyclic structures.

In certain embodiments, the metal complexes described herein may contain fluorine. In these embodiments, any one or all of substituents $R^1$, $R^2$, $R^3$, $R^4$ and $R^5$ may contain fluorine such as, for example, a fluoroalkyl, a fluoroalkyl-substituted aryl, a fluoroaryl, an alkyl-substituted fluoroalkyl, or a fluoroalkyl-substituted fluoroaryl group. In alternative embodiments, the metal complexes described herein do not contain fluorine.

In one embodiment, ligand L in formula (I) may be an alkylnitrile such as, but not limited to, CH$_2$CN or Me$_2$CH$_2$CCN. In this and the foregoing embodiments for L, the groups defined for ligand L have a hydrogen removed to allow to associate with $R^4$. In an alternative embodiment, ligand L in formula (I) may be a silylnitrile such as but not limited to Me$_2$CH$_2$SiCN. In a further embodiment, ligand L in formula (I) may be a alkyne such as but not limited to CH$_2$CCMe or CH$_2$CCH. In another embodiment, ligand L in formula (I) may be a alkene such as but not limited to Me$_3$CCHCH$_2$ or Me(CH$_2$)$_2$CHCH$_2$. In yet another embodiment, ligand L in formula (I) may be a silylalkyne having the formula (R$^9$)$_3$SiCCR$^{10}$ or (R$^{11}$)$_3$SiCCSi(R$^{11}$)$_3$ such as but not limited to Me$_3$SiCHCH, Me$_2$CH$_2$SiCHCHSiMe$_3$, (MeO)$_2$CH$_2$SiCHCH$_2$, or (EtO)$_2$CH$_2$SiCHCH$_2$. In a still further embodiment, ligand L in formula (I) may be an allene such as but not limited to CHCCCH$_2$ or MeCCCMe$_2$. In another embodiment, ligand L in formula (I) may be an alkylisocyanide such as but not limited to Me$_2$CH$_2$CNC. In the aforementioned formulas and throughout the specification, the term "Me" indicates a methyl group, "Et" indicates an ethyl group, and "i-Pr" indicates an isopropyl group.

In the above formula (I), the organometallic bond between the metal center and ligand (L) is either 2 single bonds or 1 single bond.

In one embodiment, a metal ketoiminate complex described herein where X is oxygen may be synthesized by reacting an amine functionalized with a group L with a β-diketone compound to form a β-ketoimine intermediate product. The amine may be, for example, a primary amine having the formula H$_2$NR$^4$L wherein $R^4$ and L can be anyone of the groups or atoms described above. Non-limiting examples of a primary amine having the aforementioned formula include H$_2$NCH$_2$CH$_2$OSiMe$_2$(C$_2$H$_3$). The β-diketone may be a compound having the formula R$^1$C(O) CHR$^2$C(O)R$^3$ wherein $R^1$, $R^2$, and $R^3$ can each independently be any one of the groups or atoms described above. A non-limiting example of a β-diketone compound having the aforementioned formula is 2,4-pentanedione, 1,1,1-triflouro-2,4-pentane dione, 2,4-hexanedione, and 3,5-heptanedione. One example would be reacting the amine H$_2$NCH$_2$CH$_2$OSiMe$_2$(C$_2$H$_3$) and with 2,4-pentanedione to form the β-ketoimine intermediate MeC(O)CH$_2$C (NCH$_2$CH$_2$OSiMe$_2$(C$_2$H$_3$))Me. Once the β-ketoimine intermediate product is prepared, it is deprotonated (i.e., removing the acidic proton) and then complexed with a metal source in the presence of a base to provide the complex having the above formula (I).

In another embodiment, a metal diiminate complex described herein where X is $NR^5$ as described above may be synthesized by first preparing a β-ketoimine intermediate product as described above and then treating this with an alkylating agent such as triethyloxonium tetrafluoroborate or dimethyl sulfate and then reacting the resulting compound with an R$^5$NH$_2$ where $R^5$ is as described above to yield a β-diimine salt [R$^1$C(R$^5$NH)CHR$^2$C(NR$^4$L)R$^3$]$^+$[V]$^-$ as a second intermediate product where V is the conjugate base of the alkylating agent (for example, V is a tetrafluoroborate anion when triethyloxonium tetrafluoroborate is used). The group $R^5$ may or may not have a group L bonded to it. The resulting β-diimine salt ligand is twice deprotonated and then complexed with a metal source to provide the complex having the above formula (I).

The reaction of the amine with the β-diketone compound may be conducted in the presence of a solvent. Suitable solvents include, but are not limited to, ethers (e.g. diethylether (Et$_2$O), tetrahydrofuran ("THF"), di-n-butyl ether, 1,4-dioxane, or ethylene glycol dimethyl ether); nitriles (e.g. CH$_3$CN); or aromatic compounds (e.g. toluene), alone or in admixture thereof. In certain embodiments, the solvent is THF. The reaction temperature may range from −78° C. to the boiling point of the solvent. The reaction time may range from about 0 hours or instantaneous to about 48 hours, or from about 4 to about 12 hours. In certain embodiments, the intermediate product may be purified by standard procedures such as distillation, sublimation chromatography, recrystallization, and/or trituration. In some instances, however, the reaction of the amine with the β-diketone compound may be conducted in the absence of a solvent, particularly if the resulting β-ketoimine intermediate product is a liquid.

In certain embodiments, the β-ketoimine or β-diimine intermediate product to the final metal complex may be one or more of the following there tautomeric isomers having the following formulas (II), (III), or (IV):

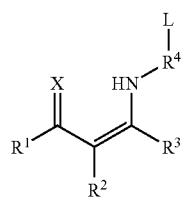

(II)

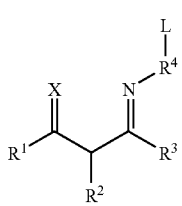

(III)

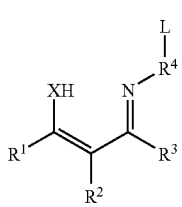

(IV)

In the above formulas, variables $R^1$, $R^2$, $R^3$, $R^4$, X and ligand (L) can each independently be any of the atoms or groups described herein.

An intermediate β-ketoimine product may need to be activated prior to its reaction with an amine or ammonia to give a β-diimine. For instance, the intermediate β-ketoimine product may first need to be alkylated by triethyloxonium tetrafluroborate or by dimethylsulfate.

Equation (IV) shows an example of one embodiment of the preparation of a metal or a Cu(I) ketoiminate complex described herein. In this embodiment, the Cu(I) complex is prepared by deprotonating the β-ketoimine intermediate product from the reaction of the amine with the β-diketone compound, or deprotonating the β-diimine intermediate product from the reaction of a β-ketoimine intermediate product with an amine or ammonia, using one or more bases and then chelating to Cu(I) to give either the β-ketoimine or β-diimine complex, respectively. A non-limiting example of this reaction is illustrated in the following equation (4) showing the preparation of a β-ketoimine Cu(I) complex:

Equation (4)

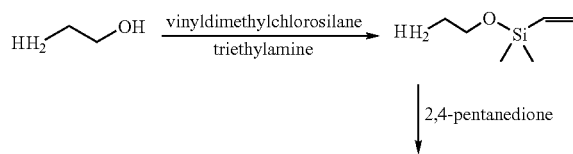

↓ 2,4-pentanedione

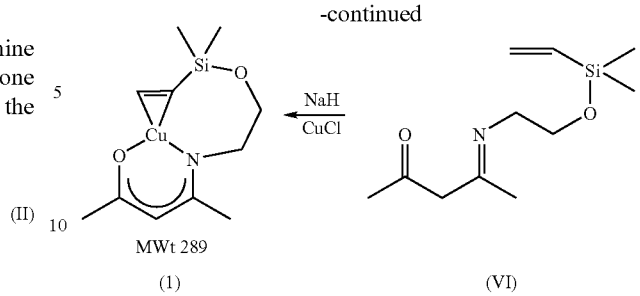

In Equation (4), the β-ketoimine intermediate product, which is a compound of formula (VI), is reacted with a base which is sodium hydride, a copper (I) source which is copper chloride to form the Cu(I) complex having the formula (I) and sodium chloride. Other bases that could be used in the above reaction include, but are not limited to, lithium hydride, n-butyl lithium, potassium hydride, sodium bis(trimethylsilylamide), lithium diisopropylamide, potassium t-butoxide, etc. Other sources of copper(I) that could be used in above reaction include, but are not limited to, copper(I) bromide, copper(I) iodide, copper(I) trifluoroacetate, copper (I) trifluoromethylsulfonate benxene adduct, copper(I) alkoxide, copper(I) amide, copper(I) acetate, copper(I) phenoxide, copper(I) acetamide, and copper(I) alkoxide. In embodiments where other metal or mixed metal complexes are prepared, the metal source is one or more metal salts containing the desired metal M. The anticipated yield of the metal or Cu(I) complex may range from about 5% to about 95% of the theoretical yield. In certain embodiments, the final product or the metal complex, such as the Cu(I) complex, may be purified by standard procedures such as distillation, sublimation, chromatography, recrystallization, and/or trituration.

Alternatively, the metal complexes of this disclosure can be prepared by first synthesizing their analogous metal bis(ketoimine) and metal bis(diimine) compounds then reacting or reducing them with a metal source. Additional alternative pathways to synthesizing these precursors are possible, as illustrated by the non-limiting cases in the examples set out below.

In alternative embodiments, the β-ketoimine intermediate product can be reacted directly with a metal source, such as copper(I) aryl (e.g., copper mesitylene) or a copper alkoxide (e.g., $[CuOt\text{-}Bu]_4$) to form a metal or Cu(I) complex. In still further embodiments, the metal complexes can be prepared from its constituent parts, i.e., the β-ketoimine intermediate product and metal atom, in a suitable electrochemical process. These same synthetic pathways may be used to synthesize the metal diiminate complexes.

Yet another example of this approach is the reaction of ethanolamine ($H_2NCH_2CH_2OH$) with 2,4-pentanedione to give the first intermediate β-ketoimine product $MeC(O)CH_2C(NCH_2CH_2OH)Me$. The first intermediate β-ketoimine product $MeC(O)CH_2C(NCH_2CH_2OH)Me$ is reacted with chlorodimethylvinylsilane to give the second intermediate β-ketoimine product $MeC(O)CH_2C(NCH_2CH_2OSiMe_2(C_2H_3))Me$. The second intermediate β-ketoimine product is deprotonated and complexed to copper to give the provide the complex $Cu(MeC(O)CHC(NCH_2CH_2OSiMe_2(C_2H_3)Me)$.

As mentioned previously, the metal complexes described herein may be used as precursors for the deposition of a film comprising copper on a substrate. Examples of suitable substrates include but are not limited to, semiconductor materials such as gallium arsenide ("GaAs"), boronitride ("BN") silicon, and compositions containing silicon such as crystalline silicon, polysilicon, amorphous silicon, epitaxial silicon, silicon dioxide ("SiO$_2$"), silicon carbide ("SiC"), silicon oxycarbide ("SiOC"), silicon nitride ("SiN"), silicon carbonitride ("SiCN"), organosilicate glasses ("OSG"), organofluorosilicate glasses ("OFSG"), fluorosilicate glasses ("FSG"), and other appropriate substrates or mixtures thereof. Substrates may further comprise a variety of layers to which the film is applied thereto such as, for example, antireflective coatings, photoresists, organic polymers, porous organic and inorganic materials, metals such as copper and aluminum, or diffusion barrier layers. The metal complexes may be deposited using any of the techniques described herein or known in the art. Exemplary deposition techniques include, but are not limited to, chemical vapor deposition (CVD), atomic layer deposition (ALD), plasma-assisted chemical vapor deposition (PACVD), and plasma-enhanced chemical vapor deposition (PECVD).

In certain embodiments, the complexes can be used to grow thin films of metal or alloys thereof by CVD or ALD by reacting with a suitable reagent. In alternative embodiments, the metal complexes may react via a disproportionation reaction to provide a metal film or metal-containing film. In still further embodiments, the metal complexes can be reacted in the presence of a reducing agent to provide a metal film or metal-containing film. For example, in one embodiment, reaction with a halogen source reagent may form a thin film of metal halide, whereas in another embodiment, reaction with a suitable oxidant such as water vapor may provide a metal oxide film. In yet another embodiment, reaction with an oxidant followed by a reducing agent such as hydrogen may form a metal film or metal/metal oxide mixed film. Alternatively, the copper precursor can be reacted with reagent gases activated by plasma either directly or downstream from a remote plasma source. The metal complexes disclosed herein can also be used mixed with other metal precursors in certain combinations to form metal films, metal-containing films, and/or metal alloy films. The films could be used as-deposited or, alternatively, could be reduced to the desired metal using a suitable reducing agent.

In certain embodiments, the metal complexes are deposited onto a substrate using a CVD or ALD technique. The deposition of the Cu(I) complexes may be conducted at temperatures of 400° C. or below, or 200° C. or below, or 100° C. or below. In a typical CVD deposition process, the metal complex having the formula (I) is introduced into a reaction chamber such as a vacuum chamber. In certain embodiments, other chemical reagents, besides the metal complex, may be introduced before, during, and/or after the introduction of the metal complex. An energy source, such as, for example, thermal, plasma or other source, energizes the metal complex and optional chemical reagents thereby forming a film on at least a portion of the substrate.

As mentioned previously, in certain embodiments, a chemical reagent may be introduced before, during, and/or after the introduction of the metal complex into the reaction chamber. The choice of chemical reagent may depend upon the composition of the desired resultant films. For example, in one embodiment, reaction with a halogen-containing chemical reagent may form a film of metal halide, whereas in another embodiment, reaction with an oxidant chemical reagent will yield a metal oxide film. Exemplary chemical reagents include, but are not limited to oxidants (i.e., $O_2$, NO, $NO_2$, $O_3$, CO, $CO_2$, etc.); water; halides; halogen-containing silanes; alkylchlorosilanes, alkylbromosilanes, or alkyliodosilanes; silicon halide compounds such as silicon tetrachloride, silicon tetrabromide, or silicon tetraiodide; halogenated tin compounds such as alkylchlorostannanes, alkylbromostannanes, or alkyliodostannanes; germane compounds such as alkylchlorogermanes, alkylbromogermanes, or alkyliodiogermanes; boron trihalide compounds such as borontrichloride, boron tribromide, or boron triodide; aluminum halide compounds such as aluminum chloride, aluminum bromide, or aluminum iodide; alkylaluminum halides; gallium halide compounds such as gallium trichloride, gallium tribromide, or gallium triodide; or combinations thereof. It is also envisioned that derivatives of the above compounds may also be used. The chemical reagents may be delivered directly as a gas to the reaction chamber, delivered as a vaporized liquid, a sublimed solid and/or transported by an inert carrier gas into the reaction chamber. Examples of inert carrier gases include nitrogen, hydrogen, argon, xenon, etc.

In certain embodiments, the metal film may form on the substrate surface by a disproportionation reaction such as that depicted for the Cu(I) complex shown in Equation 5 below.

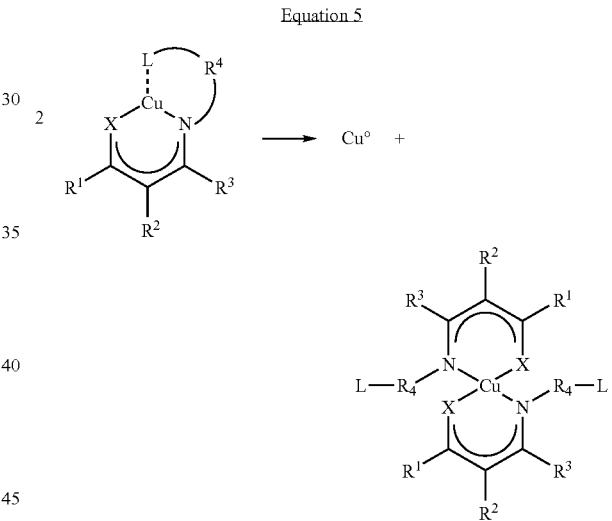

Equation 5

In another embodiment, a metal film may be deposited onto the surface of a substrate in the presence of a reducing agent to, for example, reduce the film to metal. The metal complex having the formula (I) may be introduced into a CVD or ALD reactor along with a reducing agent. The reducing agent is typically introduced in gaseous form. Examples of suitable reducing agents include, but are not limited to, hydrogen gas, alcohols, hydrogen plasma, remote hydrogen plasma, silanes (i.e., diethylsilane, ethylsilane, dimethylsilane, phenylsilane, silane, disilane, aminosilanes), boranes (i.e., borane, diborane), alanes, germanes, hydrazines, ammonia, or mixtures thereof.

In certain embodiments, a metal film is deposited from the Cu(I) complex of the formula (I) via an ALD deposition process. During a typical ALD process, one or more gaseous or vaporized precursors are introduced into the process chamber which houses the substrate in alternating pulses within a process cycle. Preferably, each process cycle forms no more than about one monolayer of material by adsorption and preferably by chemisorption. The number of process cycles used to grow the layer depends on the thickness desired but may generally exceed 1,000 cycles. For semiconductor devices, the process cycle is repeated until the barrier or seed layer within the dual damascene structure has a thickness sufficient to perform its desired function.

During ALD processing, the substrate is kept at a temperature range that facilitates chemisorption, i.e., is low enough to maintain intact bonds between adsorbed species and the underlying substrate yet high enough to avoid condensation of the precursors and to provide sufficient activation energy for the desired surface reactions in each process cycle. The process chamber temperature may range from 0° C. to 400° C., or from 0° C. to 300° C., or from 0° C. to 275° C. The pressure within the process chamber during ALD processing may range from 0.1 to 1000 Torr, of from 0.1 to 15 Torr, or from 0.1 to 10 Torr. It is understood, however, that the temperature and pressure for any particular ALD process may vary depending upon the one or more precursors involved.

Any of the aforementioned film formation methods described herein, as well as other film formation methods known in the art, may be used alone or in combination. For example, in one embodiment, a mixed composition copper-containing film may be formed by sequentially depositing a copper oxide film followed by a copper metal film and then reducing the multilayers to provide a pure copper film.

In certain embodiments, the metal complex described herein may be dissolved in a suitable solvent such as an amine (e.g., triethylamine), an ether (e.g., THF), an aromatic (e.g., toluene) or any other solvent disclosed herein, to form a solution. The resulting solution may be flash vaporized in a Direct Liquid Injection (DLI) system for vapor delivery into an ALD or CVD reaction chamber. In other embodiments, the complexes described herein can be dissolved in a stabilizing liquid such as olefins or alkynes prior to introduction to a DLI system.

EXAMPLES

In the following examples, the G.C.M.S. Spectra for the examples were performed on a Hewlett Packard 5890 Series 11 G.C. and 5972 series mass selective detector with a HP-5MS. The NMR analyses for the examples were obtained on a Bruker AMX 500 spectrometer operating at 500.MHz. Chemical shifts were set from $C_6D_6$ at 7.16 ppm in $^1H$ and 128.39 parts per million (ppm) in $^{13}C$. X-ray analysis was conducted on a Bruker D8 platform diffractometer equipped with an APEX CCD detector and a Kryoflex cryostat.

Example 1

Synthesis of $H_2NCH_2CH_2OSiMe_2(C_2H_3)$ 80.0 ml (0.57 moles) of chlorodimethylvinylsilane and 79.0 ml (0.57 moles) of triethylamine were mixed together with 2.0 liters of dry hexane and vigorously stirred under an atmosphere of nitrogen at room temperature. 35.0 ml of ethanolamine (0.57 moles) were slowly added over 1 hour resulting in a thick white slurry. The solid triethylamine hydrochloride was filtered off under nitrogen and washed with an additional 1.0 liter of dry hexane. The hexane was then distilled off at atmospheric pressure from the product, yielding 58.0 g (70%). The NMR results for the product were as follows: $^1H$ NMR: (500 MHz, $C_6D_6$): δ=0.15(d, 6H), δ=2.8(q, 2H), δ=3.5(t, 2H), δ=5.75(dd, 1H), δ=5.94(dq, 1H), δ=6.17(dq, 1H).

Example 2

Synthesis of $MeC(O)CH_2C(NCH_2CH_2OSiMe_2(C_2H_3))Me$ 58.3 g (0.40 moles) of $H_2NCH_2CH_2OSiMe_2(C_2H_3)$ were slowly added dropwise to 40 g (0.40 moles) of 2,4-pentanedione stirring in 250 ml of THF at room temperature in the presence of excess sodium sulfate. The mixture was stirred for 4 hours then the THF was stripped off under vacuum. The residual oil was then distilled at 120° C./20 mTorr to give 35 g of final product (43% yield). The NMR results for the product were as follows:

$^1H$ NMR: (500 MHz, $C_6D_6$): δ=0.15 (s, 6H), δ=1.40 (s, 3H), δ=2.0 (s, 3H), δ=2.8 q, 2H), δ=3.27 (q, 2H), δ=4.9 (s, 1H), δ=5.75 (m, 1H), δ=5.95 (m, 1H), δ=6.1 (m, 1H).

Example 3

Synthesis of $Cu(MeC(O)CHC(NCH_2CH_2OSiMe_2(C_2H_3))Me)$ 17.0 g (0.075 moles) of $MeC(O)CH_2C(NCH_2CH_2OSiMe_2(C_2H_3))Me$ were dissolved in 10.0 ml of dry tetrahydrofuran (THF) solvent and added over 1 hour to 2.5 g (40% excess at 1.04 moles) of sodium hydride stirring in 100 ml of dry THF under an atmosphere of nitrogen and allowed to stir overnight at room temperature. This mixture was filtered under nitrogen then slowly added to 7.5 g (0.075 moles) of copper(I) chloride stirring in 10 ml of dry THF at 0° C. under an atmosphere of nitrogen over a period of 1 hour after which the mixture was allowed to warm to room temperature and stir overnight. The THF was then stripped off under vacuum, 500 ml of deoxygenated dry hexane was added with stirring for 10 minutes prior to filtering. After stripping off the hexane under vacuum, the crude product was obtained as a light blue crystalline mass, yield 15.8 g (73%). Sublimation at 20 mTorr and 70° C. gave a near colorless crystalline sublimate with a melting point of 72.5° C. Sublimed crystals were submitted for X-ray analysis and a diagram of the resultant structure is provided in FIG. 1. The NMR results for the product were as follows: $^1H$ NMR: (500 MHz, $C_6D_6$): δ=0.10 (d, 6H), δ=1.53 (s, 3H), δ=2.14(s, 3H), δ=3.1 (bs, 1H), δ=3.35 (bs, 1H), δ=3.55 (bs, 1H), δ=3.65 (dd, 1H), δ=3.72 (bs, 1H), δ=3.83 (dd, 1H), δ=4.1 (dd, 1H), δ=4.96(s, 1H); $^{13}C$ NMR: (500 MHz, $C_6D_6$): δ=−2.8 (s, 1C), δ=−0.3 (s, 1C), δ=22.5 (s, 1C), δ=27.9 (s, 1C), δ=57.1 (s, 1C), δ=65.3 (s, 1C), δ=79.8 (s, 1C), δ=83.2 (s, 1C), δ=98.3 (s, 1C), δ=169.2 (s, 1C), δ=181.4 (s, 1C).

Example 4

Alternative Synthesis of $Cu(MeC(O)CHC(NCH_2CH_2OSiMe_2(C_2H_3))Me)$

The synthesis was conducted in two parts:

Part (a) Synthesis of $MeC(O)CH_2C(NCH_2CH_2OH)Me$ 100.0 g (1.0 mole) of 2,4-pentanedione were slowly added to 61.0 g (1 mole) of ethanolamine in 600 ml of vigorously stirring hexane containing 100 g of sodium sulfate drying agent. The mixture eventually became a solid mass and the hexane layer was decanted off. 600 ml of THF was then added and the mixture was slowly warmed with stirring until all the solids except the sodium sulfate were dissolved. The THF layer was then decanted off and slowly cooled overnight to crystallize. The liquid layer was then decanted off and the solid pumped dry. The yield was 87 grams or 61%. The NMR results were the intermediate product: $^{1}$H NMR (500 MHz, $C_6D_6$): δ=1.41 (s, 3H), δ=2.0 (s, 3H), δ=2.76 (q, 2H), δ=3.33 (t, 2H), δ=4.83 (s, 1H), δ=11.15 (bs, 1H).

Part (b) Synthesis of $Cu(MeC(O)CHC(NCH_2CH_2OSiMe_2(C_2H_3)Me)$ 40 g (0.28 moles) of $MeC(O)CH_2C(NCH_2CH_2OH)Me$ were dissolved in 500 ml of dry THF under an atmosphere of nitrogen and slowly added over 1 hour to 6.7 g (0.28 moles) of sodium hydride stirring in 250 ml of THF. Hydrogen gas was seen to evolve and the mixture became a thick white slurry. To this was added 112 ml of 2.5M n-butyl lithium (0.28 moles) over 1 hour at which point 250 ml of additional THF was added to enable better mixing. The resulting pale yellow suspension was stirred for two more hours after which 33.6 g (0.28 moles) of chlorodimethylvinylsilane was added over 30 minutes and this mixture was stirred for another 2 hours. This thick suspension was then added dropwise over 1 hour to 29 g (0.28 moles) of copper(I) chloride stirring in 50 ml of dry THF at 0° C. under an atmosphere of nitrogen. The mixture was then allowed to warm to room temperature with stirring overnight. The THF was then stripped off under vacuum and 500 ml of dry hexane added under nitrogen, the mixture stirred for 10 minutes, then the hexane was filtered off from the solids. An additional 500 ml of hexane was added to the solids and warmed to 45° C. with stirring for 45 minutes prior to filtering and combining with the first hexane extract. The hexane was stripped off under vacuum to give 52.0 g of pale blue crude crystalline product and the percentage yield was 64%. The crude product was then purified by sublimation at 70° C. and 20 mTorr.

Example 5

Synthesis of $MeC(O)CH_2C(NCH_2CH_2NMeH)Me$ 20.0 g (0.2 moles) of 2,4-pentanedione were added dropwise over a 30 minute period to 14.8 g (0.2 moles) of N-methylethylenediamine in 200 ml of THF stirring with 36 g of sodium sulfate drying agent. The mixture became yellow colored and was stirred for two days at room temperature. The THF later was then decanted off and stored overnight over dried 2A molecular sieves before stripping off the THF under vacuum to give a golden brown oil. The yield was 25.5 g or 82%. The NMR results for the product were: $^{1}$H NMR (500 MHz, $C_6D_6$): δ=1.45 (s, 3H), δ=2.03 (s, 3H), δ=2.05 (s, 3H), δ=2.25 (t, 2H), δ=2.74 (q, 2H), δ=4.88 (s, 1H), δ=11.1 (bs, 1H).

Example 6

Synthesis of $MeC(O)CH_2C(NCH_2CH_2NMeSiMe_2(C_2H_3))Me$ 51.0 g (0.327 moles) of $MeC(O)CH_2C(NCH_2CH_2NMeH)Me$ were added over 1 hour to 13.1 g (0.327 moles) of potassium hydride stirred in 1 liter of dry THF under a nitrogen atmosphere to give a thick cream colored suspension. To this was added 45 ml (0.327 moles) of chlorodimethylvinylsilane over a 30 minute period and the mixture was then stirred for an additional two hours. The THF was then stripped off under vacuum and one liter of dry hexane added with stirring for 10 minutes. This suspension was then filtered and the solid was washed three times with 50 ml of additional hexane. All the hexane washings were combined and then stripped down to give 62.3 grams, or 80% yield, of a golden brown oil which was then vacuum distilled at 120° C. and 20 mTorr. The NMR results for the product were: $^{1}$H NMR (500 MHz, $C_6D_6$): δ=0.18 (s, 6H), δ=1.44 (s, 3H), δ=2.04 (s, 3H), δ=2.24 (s, 3H), δ=2.57 (t, 2H), δ=2.71 (q, 2H), δ=4.9 (s, 1H), δ=5.7 (dd, 1H), δ=5.94 (dd, 1H), δ=6.2 (dd, 1H), δ=11.1 (bs, 1H).

Example 7

Figure 2:
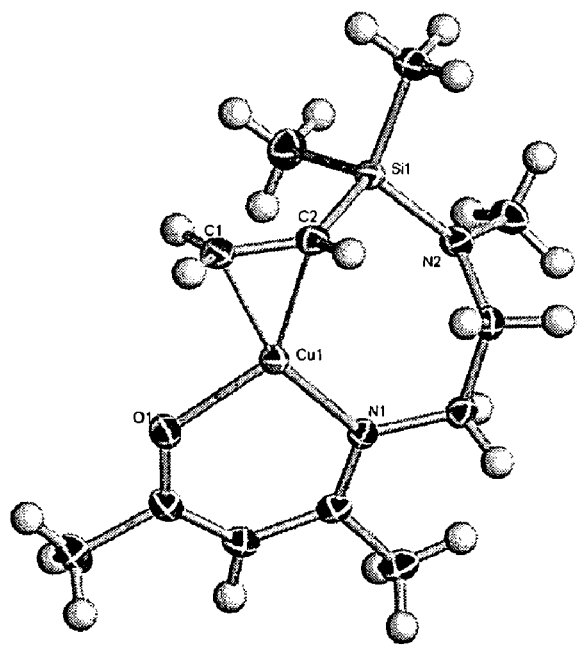
FIG. 2 provides an exemplary structure of another embodiment of the metal complexes described herein or $Cu(MeC(O)CHC(NCH_2CH_2NMeSiMe_2(C_2H_3))Me)$

Synthesis of $Cu(MeC(O)CHC(NCH_2CH_2NMeSiMe_2(C_2H_3))Me)$ 6.1 g (0.025 moles) of $MeC(O)CH_2C(NCH_2CH_2NMeSiMe_2(C_2H_3))Me$ were added over 30 minutes to 1.02 g (0.025 moles) of potassium hydride stirring in 175 ml of dry THF under a nitrogen atmosphere and stirred for 2 hours. The faintly turbid solution was then filtered and added dropwise over a three hour period to 2.5 g (0.025 moles) of copper (I) chloride stirring in 10 ml of dry THF at 0° C. under an atmosphere of nitrogen. The mixture was then allowed to warm to room temperature overnight. The THF was then stripped under vacuum, 200 ml of dry hexane under nitrogen was then added, the mixture stirred for 5 minutes then filtered. Stripping off the hexane yielded 6.3 g of light jade green crystalline crude product, or a yield of 83%, which was purified by sublimation at 75° C. and 20 mTorr. The melting point of the product was 86° C. Sublimed crystals were submitted for X-ray analysis to yield FIG. 2. The NMR results for the product were as follows: 1H NMR: (500 MHz, $C_6D_6$): δ=0.05 (bs, 6H), δ=1.65 (s, 3H), δ=2.16 (s, 3H), δ=2.27 (s, 3H), δ=2.47 (bs, 1H), δ=2.76 (bs, 1H), δ=3.11 (bs, 1H), δ=3.21 (bs, 1H), δ=3.78 (dd, 1H), δ=4.0 (dd, 1H), δ=4.21 (dd, 1H), δ=5.01 (s, 1H); and $^{13}$C NMR: (500 MHz, $C_6D_6$): δ=−0.05 (bs, 1C), δ=−2.5 (bs, 1C), δ=23.4 (s, 1C), δ=27.9 (s, 1C), δ=34.9 (s, 1C), δ=51.6 (s, 1C), δ=53.0 (s, 1C), δ=81.2 (s, 1C), δ=84.1 (s, 1C), δ=170.1 (s, 1C), δ=180.8 (s, 1C).

Example 8

Alternative Synthesis of $Cu(MeC(O)CHC(NCH_2CH_2NMeSiMe_2(C_2H_3))Me)$ 1.625 g (0.0104 moles) of $MeC(O)CH_2C(NCH_2CH_2NMeH)Me$ were added over 30 minutes to 0.417 g (0.0104 moles) of potassium hydride stirred in 100 ml of dry THF under an atmosphere of nitrogen to give a thick white paste. To this was added 4.2 ml of 2.5M n-butyl lithium (0.0104 moles) over 5 minutes giving a clear yellow/orange solution. To this was added 1.4 ml of chlorodimethylvinylsilane (0.01 moles). The mixture now became turbid and was stirred for another 20 minutes. This slurry was then added over 30 minutes dropwise to 1.04 g (0.0104 moles) of copper(I) chloride stirred in 5 ml dry THF at 0° C. under nitrogen then allowed to warm to room temperature and stir overnight. The THF was stripped off under vacuum and 100 ml of dry hexane was added under nitrogen. The mixture was filtered and then stripped of hexane to yield a crude product, or $Cu(MeC(O)CHC(NCH_2CH_2NMeSiMe_2(C_2H_3))Me)$, which was identified by GCMS.

I claim:
1. A metal complex represented by formula (I):

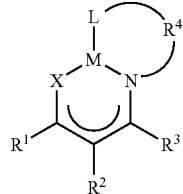

wherein M is a metal selected from Cu, Au, Ag, Co, Ru, Rh, Pt, In, Pd, Ni, and Os;
wherein X is selected from oxygen and $NR^5$;
wherein $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;
wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;
wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R_{12})_3SiCR^{13}C(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR_{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond.

2. The complex of claim 1 wherein M is Cu.
3. The complex of claim 1, wherein X is O.
4. The complex of claim 3 wherein at least one of substituents $R^1$, $R^2$, and/or $R^3$ connects with $R^4$ provided that $R^1$, $R^2$, and/or $R^3$ are not the hydrogen atom, the halogen atom, or the nitro group having the formula $NO_2$.
5. The complex of claim 1 wherein at least one of substituents $R^1$, $R^2$, and/or $R^3$ connects with $R^4$ to form a cyclic structure.
6. The complex of claim 1 wherein X is $NR^5$.
7. The complex of claim 6 wherein $R^5$ is associated with ligand L and a hydrogen, an atom, or a group removed.
8. The complex of claim 7 wherein the complex has an additional ligand L associated with $R^5$.
9. The complex of claim 6 wherein at least one of substituents $R^1$, $R^2$, $R^3$, and/or $R^5$ connects with $R^5$ provided that $R^1$, $R^2$, $R^3$ and/or $R^5$ are not the hydrogen atom, the halogen atom, or the nitro group having the formula $NO_2$.
10. The complex of claim 1 wherein at least one of substituents $R^1$, $R^2$, and/or $R^3$ connects with $R^5$ to form a cyclic structure.
11. A method for depositing a film comprising metal on a substrate, the method comprising:
contacting the substrate with a metal complex having formula (I) wherein the contacting is conducted at conditions sufficient for the complex to react and form the film

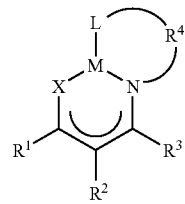

wherein M is a metal selected from Cu, Au, Ag, Co, Ru, Rh, Pt, In, Pd, Ni, and Os;

wherein X is selected from oxygen and $NR^5$;

wherein $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;

wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;

wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R_{12})_3SiCR^{13}C(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond.

12. An electronic device comprising a film comprising copper wherein the film is deposited from a precursor mixture comprising a metal complex having formula (I):

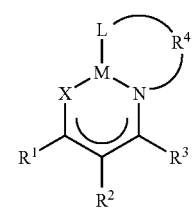

wherein M is a metal selected from Cu, Au, Ag, Co, Ru, Rh, Pt, In, Pd, Ni, and Os;

wherein X is selected from oxygen and $NR^5$;

wherein $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;

wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;

wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond.

13. A method of making a metal complex having formula (I):

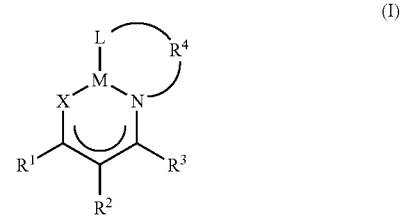

wherein M is a metal selected from Cu, Au, Ag, Co, Ru, Rh, Pt, In, Pd, Ni, and Os;

wherein X is oxygen;

wherein $R^1$, $R^2$, and $R^3$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aWl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;

wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;

wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, an aryl, a vinyl, or an amide comprising from 1 to 20 carbon atoms and R13 is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond, the method comprising:

providing a primary amine having a formula $H_2NR^4L$;

condensing the primary amine with a β-diketone compound having a formula $R^1C(O)CHR^2C(O)R^3$ to provide a β-ketoimine intermediate product having a formula $R^1C(O)CHR^2CNR^4LR^3$; and deprotonating the β-ketoimine intermediate product using a base in the presence of a metal source to form the metal complex.

14. A method of making a metal complex having formula (I):

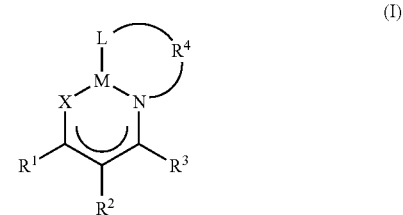

wherein M is a metal selected from Cu, Au, Ag, Co, Ru, Rh, Pt, In, Pd, Ni, and Os;

wherein X is $NR^5$;

wherein $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;

wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;

wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and
wherein an organometallic bond between M and L is selected from two single bonds or one single bond, the method comprising:
providing a primary amine having a formula $H_2NR^4L$;
reacting the primary amine with a β-diketone compound having a formula $R^1C(O)CHR^2C(O)R^3$ to provide a β-ketoimine intermediate product having a formula $R^1C(O)CHR^2CN(R^4)(L)R^3$; and
treating the β-ketoimine intermediate product within an alkylating agent and reacting with $R^5NH_2$ to provide a salt having a formula $R^1C(R^5NH)CHR^2C(NR^4L)R^3]^+[V]^-$ where V is a conjugate base of the alkylating agent; and
deprotonating the β-ketoimine intermediate product a plurality of times using a base in the presence of a metal source to form the metal complex.

15. A method of making a metal complex having formula (I):

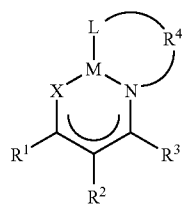

(I)

wherein M is a metal selected from Cu, Au, Ag, Co, Ru, Rh, Pt, In, Pd, Ni, and Os;
wherein X is oxygen;
wherein $R^1$, $R^2$, and $R^3$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;
wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein (x+y)=2n, (w+z)=(2m+1), and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;
wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond, the method comprising:

providing a primary amine having a formula $H_2NR^4$;

condensing the primary amine with a β-diketone compound having a formula $R^1C(O)CHR^2C(O)R^3$ to provide a first β-ketoimine intermediate product having a formula $R^1C(O)CHR^2CN(R^4)R^3$;

attaching ligand (L) to the first β-ketoimine intermediate product to provide a second intermediate product having a formula $R^1C(O)CHR^2CN(R^4)LR^3$; and deprotonating the second β-ketoimine intermediate product using a base in the presence of a metal source to form the metal complex.

16. $Cu(MeC(O)CHC(NCH_2CH_2OSiMe_2(C_2H_3))Me)$.

17. $Cu(MeC(O)CHC(NCH_2CH_2NSiMe_2(C_2H_3))Me)$.

18. A metal complex represented by a following formula:

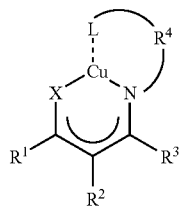

wherein X is selected from oxygen and $NR^5$;

wherein $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein $(x+y)=2n$, $(w+z)=(2m+1)$, and n and m are each independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;

wherein $R^4$ is selected from an alkyl having a formula $C_nH_{2n+1}$ wherein n is a number ranging from 1 to 20; a fluoroalkyl having the formula $C_nH_xF_y$ wherein the product of the (x+y) equals the product of (2n+1) and n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a fluoroalkyl substituted aryl comprising from 6 to 12 carbon atoms; a fluoroaryl comprising from 6 to 12 carbon atoms; an ether having a formula $(CH_2)_nO(C_mH_{2m+1})$ where n and m are independently a number ranging from 1 to 20; a fluoroether having a formula $(C_nH_xF_y)O(C_mH_wF_z)$ wherein $(x+y)=2n$, $(w+z)=(2m+1)$, and n and m are each independently a number ranging from 1 to 20; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;

wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond.

* * * * *

UNITED STATES PATENT AND TRADEMARK OFFICE
CERTIFICATE OF CORRECTION

PATENT NO. : 7,205,422 B2  
APPLICATION NO. : 11/111452  
DATED : April 17, 2007  
INVENTOR(S) : John A. T. Norman Page 1 of 2

It is certified that error appears in the above-identified patent and that said Letters Patent is hereby corrected as shown below:

Column 22, Line 18

In claim 11 delete the word "$SiCR_{13}CR^{13}Si(R^{14})_3$" and insert the word -- $SiCR^{13}CR^{13}Si(R^{14})_3$ --

Column 23, Line 53

In claim 12 delete the word "$(R_{12})_3SiCR^{13}CR$" and insert the word -- $(R^{12})_3SiCR^{13}C$ --

Column 23, Line 60

In claim 12 delete the word "$SiCR_{13}CR^{13}Si(R^{14})_3$" and insert the word -- $SiCR^{13}CR^{13}Si(R^{14})_3$ --

Column 25, Line 27

In claim 13 delete the word "$(R_{12})_3SiCR^{13}C$" and insert the word -- $(R^{12})_3SiCR^{13}C$ --

Column 25, Line 30

In claim 13 delete the word "R13" and insert -- $R^{13}$ --

Column 25, Line 34

In claim 13 delete the word "$SiCR_{13}CR^{13}Si(R^{14})_3$" and insert the word -- $SiCR^{13}CR^{13}Si(R^{14})_3$ --

Column 27, Line 13

In claim 14 delete the word "$(R_{12})$" and insert the word -- $(R_{12})$ --

UNITED STATES PATENT AND TRADEMARK OFFICE
CERTIFICATE OF CORRECTION

PATENT NO.       : 7,205,422 B2
APPLICATION NO.  : 11/111452
DATED            : April 17, 2007
INVENTOR(S)      : John A. T. Norman It is certified that error appears in the above-identified patent and that said Letters Patent is hereby corrected as shown below:

Column 27, Line 20

In claim 14 delete the word "$SiCR_{13}CR^{13}Si(R^{14})_3$" and insert the word
-- $SiCR^{13}CR^{13}Si(R^{14})_3$ --

Column 28, Line 66

In claim 15 delete the word "$(R_{12})_3SiCR^{13}C$" and insert the word -- $(R^{12})_3SiCR^{13}C$ --

Column 29, Line 6

In claim 15 delete the word "$SiCR_{13}CR^{13}Si(R^{14})_3$" and insert the word
-- $SiCR^{13}CR^{13}Si(R^{14})_3$ --

Column 30, Line 48

In claim 18 delete the words "$(R_{12})_3SiCR^{13}$" and insert the word -- $(R^{12})_3SiCR^{13}$ --

Column 30, Line 55

In claim 18 delete the word "$SiCR_{13}CR^{13}Si(R^{14})_3$" and insert the word
-- $SiCR^{13}CR^{13}Si(R^{14})_3$ --

Signed and Sealed this

Third Day of July, 2007

JON W. DUDAS
*Director of the United States Patent and Trademark Office*